US012576216B2

(12) United States Patent
Cho et al.

(10) Patent No.: US 12,576,216 B2
(45) Date of Patent: Mar. 17, 2026

(54) DISPOSABLE INJECTION DEVICE WITH LOCKING STRUCTURE TO PREVENT REUSE

(71) Applicant: POONGLIM PHARMATECH INC., Jeollabuk-do (KR)

(72) Inventors: Hee Min Cho, Jeollabuk-do (KR); Jong Deok Yun, Jeollabuk-do (KR)

(73) Assignee: POONGLIM PHARMATECH INC., Jeollabuk-do (KR)

( * ) Notice: Subject to any disclaimer, the term of this patent is extended or adjusted under 35 U.S.C. 154(b) by 331 days.

(21) Appl. No.: 17/510,825

(22) Filed: Oct. 26, 2021

(65) Prior Publication Data

US 2022/0184323 A1     Jun. 16, 2022

(30) Foreign Application Priority Data

Dec. 11, 2020    (KR) ........................ 10-2020-0172884

(51) Int. Cl.
| *A61M 5/50* | (2006.01) |
| *A61M 5/315* | (2006.01) |
| *A61M 5/32* | (2006.01) |

(52) U.S. Cl.
CPC ........ *A61M 5/502* (2013.01); *A61M 5/31511* (2013.01); *A61M 5/3243* (2013.01); *A61M 5/3271* (2013.01)

(58) Field of Classification Search
CPC .. A61M 5/502; A61M 5/3245; A61M 5/3243; A61M 5/3137; A61M 5/3202; A61M 5/326; A61M 2005/3261; A61M 2005/3264; A61M 2005/3139; A61M 2005/312; A61M 2005/3247
See application file for complete search history.

(56) References Cited

U.S. PATENT DOCUMENTS 4,994,045 A  *  2/1991  Ranford .............. A61M 5/3271
                                                              604/263
10,086,149 B2 *  10/2018  Dugand .............. A61M 5/3245

FOREIGN PATENT DOCUMENTS

| EP | 3 388 098 A1 | 10/2018 |
| KR | 20-0458761 Y1 | 3/2012 |

* cited by examiner

*Primary Examiner* — Michael J Tsai
*Assistant Examiner* — Justin L Zamory
(74) *Attorney, Agent, or Firm* — The PL Law Group, PLLC

(57) ABSTRACT

A disposable injection device according to an embodiment has a locking structure to prevent reuse in which, in a state where a locking module accommodating a liquid cartridge in which the injection of an injection solution is completed is additionally pressed, when the pressing force is removed, the pressed locking module is raised and lowered due to a restoring force of an elastic spring located in a compressed state at a lower end of the locking module and locked to an outer housing, and thus the locking module is prevented from being further pressed, and smoothly separates the locking module from the outer housing through a separation guide portion having a tapered shape and formed on an upper end of the outer housing through a pressure head constituting an upper portion of a pressurizing piston unit in a state where in the injection of the injection solution is completed.

2 Claims, 7 Drawing Sheets

DISPOSABLE INJECTION DEVICE WITH LOCKING STRUCTURE TO PREVENT REUSE

CROSS REFERENCE TO RELATED APPLICATIONS AND CLAIM OF PRIORITY

This application claims the benefit under 35 USC § 119(a) of Korean Patent Application No. 10-2020-0172884, filed on Dec. 11, 2020, in the Korean Intellectual Property Office, the entire disclosure of which is incorporated herein by reference for all purposes.

BACKGROUND

1. Technical Field

The present disclosure relates to a disposable injection device with a locking structure to prevent reuse, and more particularly, to a disposable injection device in which, after the injection of an injection solution contained in a liquid cartridge of a disposable syringe is completed, when a locking module accommodating the pressed liquid cartridge is raised and lowered due to an extension force of a compressed elastic spring and is locked to an outer housing, the locking module and the liquid cartridge may be prevented from being pressed and thus reuse of the disposable syringe may be prevented.

2. Background Art

In general, a syringe is one of medical supplies, and is used for various purposes such as injecting an injection solution, collecting blood, or collecting a sample.

A syringe includes a syringe barrel in which an injection solution is contained, a syringe plunger pushed or pulled along the inside of the syringe barrel to inject the injection solution or collect blood or a sample, a syringe needle connected to a discharge orifice at an upper end of the syringe barrel and configured to inject the injection solution into the skin, and a syringe cap configured to protect the syringe needle, and may be used by coupling a blood collection tool, the syringe cap, or the syringe needle to the discharge orifice at the upper end of the syringe barrel depending on the purpose of use.

In principle, a syringe should be used once. Because a patient's bloodstains remain on a needle of a used syringe, and when the used syringe is used again, pathogens (e.g., hepatitis or AIDS) contained in the bloodstains of the patient may spread to other people and cause secondary infections, a syringe should be used only once and disposed of.

However, there are cases, for convenience reasons or to reduce the cost of purchasing a syringe, a syringe that has been used once is reused without discarding it, and even a syringe that has been used several times is reused because a patient is unable to easily identify whether the syringe has already been used. Such reuse of syringes has become a social problem, and a number of medical accidents, including a mass outbreak of hepatitis C, have occurred.

To name a few representative examples, drug addicts frequently reuse syringes when injecting drugs in places other than medical institutions, and some medical institutions often reuse disposable syringes for economic reasons to reduce the cost of consumables.

As a result, the risk of infections due to reused syringes increases, and furthermore, social problems such as the spread of disease through the blood of others are caused.

Accordingly, various technologies for preventing reuse have been devised.

For example, Patent Registration No. 10-1750352 discloses a syringe cap having a reuse prevention structure, including a reuse prevention cover which fixes a fixed body to a front end of a syringe by fusion or welding, combines a separable body with the fixed body by a screw, and entirely covers the separable body and the fixed body, wherein the reuse prevention cover includes an upper body fitted over an outer surface of the separable body and a lower body fitted over surround an outer surface of the fixed body. The upper body and the lower body are integrally connected to each other by a connection breakable portion, and the connection breakable portion may be broken by both an external force caused by a rotary motion of the upper body in one direction relative to the lower body and a pushing-up motion of the separable body from the fixed body such that the upper body and the separable body are respectively separated from the lower body and the fixed body. Because it may be determined whether the syringe is usable by checking whether the connection breakable portion is broken, reuse of the syringe may be prevented. Because the fixed body is stably fixed to the syringe, the upper body of the reuse prevention cover may be easily separated from the lower body, and safety accidents caused by the connection breakable portion may be prevented.

However, the prior art has problems in that, because the separable body separated from the fixed body is divided into the upper body, the connection breakable portion should be broken to separate the upper body from the lower body, and reuse is prevented by whether the upper body and the lower body are separated before use, a syringe needle coupling portion of the syringe which has been used once is exposed to the outside as it is and a syringe plunger may still be pressed, thereby failing to completely prevent reuse of the disposable syringe.

SUMMARY

An objective of the present disclosure is to provide a disposable injection device which may smoothly separate a locking module from an outer housing through a process of opening outward separation guide portions having a tapered shape and formed on an upper end of the outer housing through a pressure head constituting an upper portion of a pressurizing piston unit, in a state where the injection of an injection solution is completed.

Also, the present disclosure has a locking structure to prevent reuse in which, in a state where the locking module accommodating a liquid cartridge in which the injection of an injection solution is completed is additionally pressed, when the pressing force is removed, the pressed locking module is raised and lowered due to a restoring force of an elastic spring that is located in a compressed state at a lower end of the locking module and is locked to the outer housing, and thus the locking module may be prevented from being further pressed.

Also, the present disclosure provides a structure in which a syringe needle coupled to a lower end of the liquid cartridge is drawn and located inside the outer housing and thus reuse of a disposable syringe may be reliably prevented.

A disposable injection device according to the present disclosure for achieving the objectives includes an outer housing 100, a locking module 200 structured to be positionchangeably coupled in the outer housing 100, an elastic spring 10 located in a compressed state at a lower end of the locking module 200 in the outer housing 100, a liquid cartridge 20 coupled to the locking module 200 and containing an injection solution therein, and a pressurizing piston unit 30 configured to pressurize the inside of the liquid cartridge 20 and discharge the injection solution, wherein the outer housing 100 includes a housing body 110 having a hollow shape with an open upper portion, a pair of separation guide portions 120 constituting the open upper portion of the housing body 110, and a reuse preventing portion 130 formed on a side surface of the housing body 110, the locking module 200 includes a locking body 210 position-changeably located in the housing body 110, a cartridge coupling portion 220 constituting an upper portion of the locking body 210, and a locking portion 230 protruding from an outer surface of the locking body 210, and the pressurizing piston unit 30 includes a pressure head 31, a separation plate 32 located in a plate shape under the pressure head 31 and configured to allow the pair of separation guide portions 120 to be opened outward, and a plunger 33 longitudinally formed from a lower portion of the pressure head 31 and slidably coupled into the cartridge body 21, wherein, when the pressurizing piston unit 30 is lowered, fixing between the locking module 200 and the outer housing 100 is temporarily released through a structure in which the separation plate 32 moves along a protrusion inclined surface 124 that is an inner side of a separation guide protrusion 123 of the separation guide portion 120.

Unlocking protrusions 211 formed on both side surfaces of the locking body 210 may be coupled to protrusion mount grooves 134 of the reuse preventing portion 130 to fix a position of the locking body 210 in the outer housing 100.

As described above, the present disclosure may have a locking structure to prevent reuse in which, in a state where a locking module accommodating a liquid cartridge in which the injection of an injection solution is completed is additionally pressed, when the pressing force is removed, the pressed liquid cartridge is raised and lowered due to a restoring force of an elastic spring that is located in a compressed state at a lower end of the liquid cartridge and is locked to an outer housing, and thus the locking module accommodating the liquid cartridge is prevented from being further pressed. Also, the present disclosure may smoothly separate the locking module from the outer housing through a separation guide portion having a tapered shape and formed on an upper end of the outer housing through a pressure head constituting an upper portion of a pressurizing piston unit that is slidably coupled to the liquid cartridge and thus may reliably prevent reuse of a disposable syringe by enabling a syringe needle coupled to the lower end of the liquid cartridge to be drawn and located inside the outer housing.

DETAILED DESCRIPTION

Figure 1:
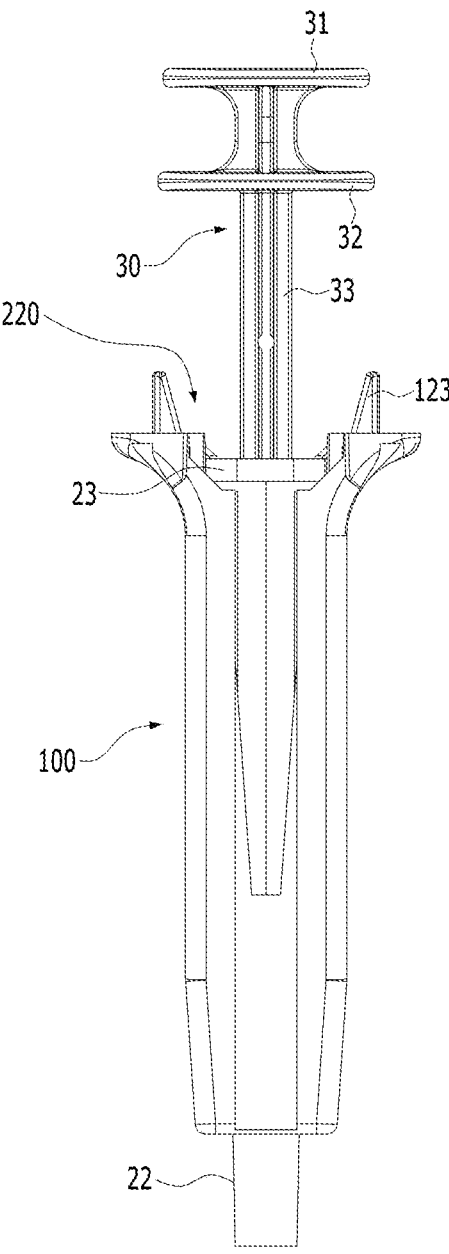
FIG. 1 illustrates that a locking module accommodating a liquid cartridge is completely accommodated in an outer housing before a syringe is used, in a disposable injection device with a locking structure to prevent reuse according to the present disclosure.

Hereinafter, embodiments of the present disclosure will be described in more detail with reference to the drawings. The present disclosure may, however, be embodied in many different forms and should not be construed as being limited to the embodiments set forth herein; rather, these embodiments are provided so that this disclosure will be thorough and complete, and will fully convey the concept of the present disclosure to one of ordinary skill in the art. In the drawings, the same reference numerals denote the same elements.

In adding reference numerals to elements of each drawing, it should be noted that the same elements are denoted by the same reference numerals as much as possible even when they are indicated on different drawings. Also, in describing the present disclosure, detailed descriptions of related well-known functions or configurations that may blur the points of the present disclosure are omitted.

Hereinafter, a disposable injection device with a locking structure to prevent reuse according to an embodiment of the present disclosure will be described with reference to FIGS. 1 through 7.

The disposable injection device includes an outer housing 100 configured to fix a locking module 200 to prevent additional use of the locking module 200 in a state where an injection solution is used up, the locking module 200 position-changeably coupled in the outer housing and structured to prevent reuse, an elastic spring 10 located in an initially compressed state at a lower end of the locking module 200 in the outer housing 100, a liquid cartridge 20 fixedly coupled to the locking module 200 and containing an injection solution therein, and a pressurizing piston unit 30 configured to pressurize the inside of the liquid cartridge and including a pressure plunger 33 and a pressure head 31.

The elastic spring 10 has an elastic body having a coil shape, and primarily supports the locking module 200 in the initially pressed state. Next, the pressurizing piston unit 30 secondarily pushes upward the locking module 200 that is temporarily released in the outer housing 100.

The liquid cartridge 20 includes a cartridge body 21 in which an injection solution is contained, a needle coupling portion 22 coupled to a lower end of the cartridge body 21 and configured to allow the injection solution contained in the cartridge body 21 to be injected into the skin through a syringe needle when the pressurizing piston unit 30 is lowered along the inside of the cartridge body 21, and a locking portion coupling plate 23 coupled to an upper end of the cartridge body 21 and configured to guide the liquid cartridge 20 to be fixed to the locking module 200 without shaking.

The pressurizing piston unit 30 includes the pressure head 31 constituting an upper end portion, a separation plate 32 located in a plate shape under the pressure head 31 and configured to allow separation guide portions 120 constituting an upper portion of the outer housing 100 to be opened outward, the plunger 33 longitudinally formed from a lower portion of the pressure head 31 and slidably coupled into the cartridge body 21, and a pressure end 35 located on a lower end of the plunger 33.

When the pressurizing piston unit 30 is pressed, the plunger 33 and the pressure end 35 are pressed to a lower portion of the outer housing 100, the injection solution contained in the liquid cartridge 20 is pushed to the needle coupling portion 22, and the injection solution is injected into the skin through the syringe needle coupled to the needle coupling portion 22. In this case, the elastic spring 10 is maintained in the compressed state.

According to the present disclosure, the pressurizing piston unit 30 is pressed, the plunger 33 is lowered inside the cartridge body 21 in which the injection solution is contained, and the injection solution contained in the cartridge body 21 is injected into the skin through the syringe needle coupled to the needle coupling portion 22, which are well known and thus a detailed description thereof will be omitted.

The outer housing 100 includes a housing body 110 having a hollow shape with an open upper portion, a pair of separation guide portions 120 constituting the open upper portion of the housing body 110, and a reuse preventing portion 130 formed on a side surface of the housing body 110.

The housing body 110 has a volume large enough to accommodate the locking module 200, and in order for the pair of separation guide portions 120 facing each other to be temporarily opened outward by the pressurizing piston unit 30, a certain space is formed in a side surface of the housing body 110 based on the pair of separation guide portions 120.

Each of the pair of separation guide portions 120 includes a separation guide plate 121 extending outward from an upper end of the housing body 110 and a separation guide protrusion 123 extending upward from a top surface of the separation guide plate 121 and including a protrusion inclined surface 124 as an inner surface.

The reuse preventing portion 130 includes a slide groove 131 longitudinally formed in a vertical direction in the housing body 110, protrusion grooves 132 formed on both sides of an upper portion of the slide groove 131 to be spaced apart from each other, a lowering preventing protrusion 133 configured to connect an upper end of the slide groove 131 to an upper end of the protrusion groove 132, and a protrusion mount groove 134 formed over the lowering preventing protrusion 133 and passing through the housing body 110.

The slide groove 131 functions to guide a movement when the locking module 200 accommodated in the outer housing 100 is temporarily released and raised. That is, the slide groove 131 functions to guide the locking module 200 that is temporarily released to move to a location where the locking module 200 is locked again.

The protrusion grooves 132 may secure a space for flexible movement of the lowering preventing protrusion 133.

The lowering preventing protrusion 133 functions to prevent the raised locking module 200 from being lowered again. The lowering preventing protrusion 133 is bent inward and has a stepped shape with an inclined lower end.

The protrusion mount groove 134 for fixing the position of the locking module 200 may primarily fix the position of the locking module 200 by being coupled to an unlocking protrusion 211 formed on an outer surface of the locking module 200, and may prevent further raising by being coupled to a locking portion 230 of the locking module 200 during temporary position release and secondary position fixing of the locking module 200 through a process in which the pair of separation guide portions 120 are opened outward by the pressurizing piston unit 30.

The locking module 200 includes a locking body 210 position-changeably located in the housing body 110, a cartridge coupling portion 220 constituting an upper portion of the locking body 210, and the locking portion 230 protruding from an outer surface of the locking body 210.

The locking body 210 has a hollow shape with an open upper portion accommodated in the housing body 110. An upper end of the elastic spring 10 is fastened to a lower end of the locking body 210. The unlocking protrusions 211 are formed on both side surfaces of the locking body 210. When the unlocking protrusions 211 are coupled to the protrusion mount grooves 134 of the reuse preventing portion 130, the position of the locking body 210 in the outer housing 100 may be fixed.

The cartridge coupling portion 220 includes a coupling frame 221 located on an upper end of the locking body 210, a partition wall 222 formed in a vertical direction in an inner space of the coupling frame 221, and a cartridge fixing latch 223 located in each of spaces separated by the partition wall to have a certain elasticity. When the liquid cartridge 20 is fixed to the locking module 200, an upward movement of the locking portion coupling plate 23 of the liquid cartridge 20 is limited by the cartridge fixing latch 223, thereby preventing the liquid cartridge 20 to be separated from the locking module 200.

The locking portion 230 includes locking protrusions 231 protruding from both side surfaces of the locking body 210 to be located under the unlocking protrusions 211 and be spaced apart from the unlocking protrusions 211, a locking stepped portion 232 constituting a lower end of the locking protrusion 231, a locking body 233 extending downward from the locking protrusion 231 based on the locking stepped portion 232, and protrusion moving grooves 235 formed on both sides of the locking body 233. During secondary position fixing after temporary position release of the locking module 200 through a process in which the pair of separation guide portions 120 are opened outward by the pressurizing piston unit 30, the locking protrusion 231 of the locking portion 230 is caught by an upper end of the lowering preventing protrusion 133, thereby limiting lowering of the locking module 200.

Figure 2:
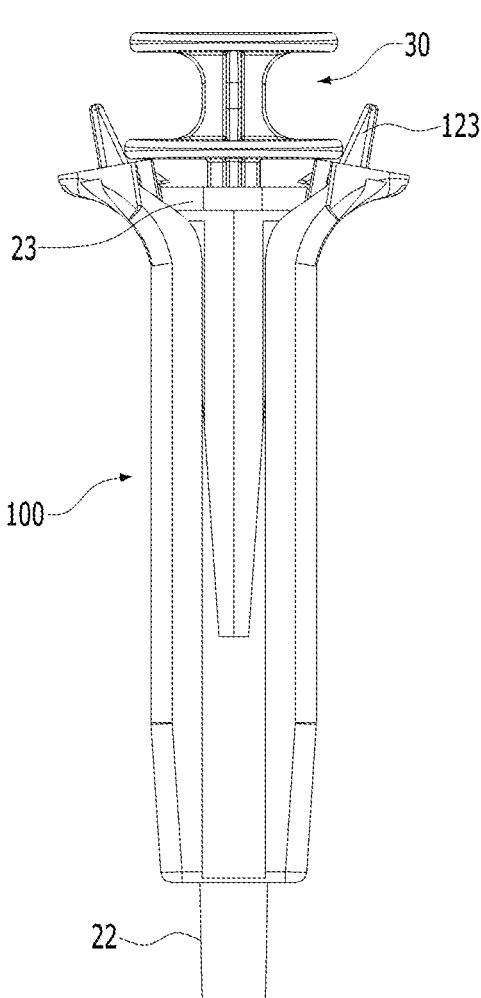
FIG. 2 illustrates a time when a pressurizing piston unit is completely lowered to guide separation between the locking module and the outer housing, in the disposable injection device with the locking structure to prevent reuse according to the present disclosure.
Figure 3:
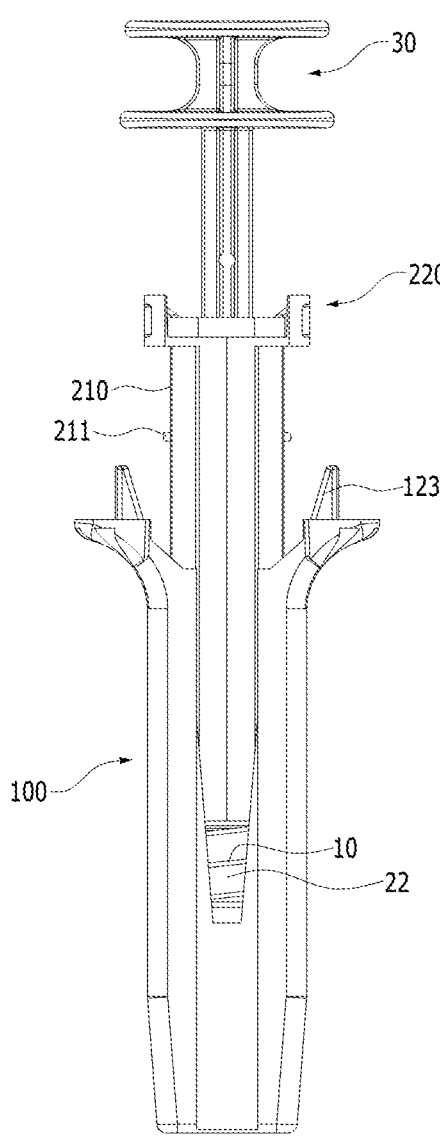
FIG. 3 illustrates a state where the locking module accommodating the liquid cartridge is raised and lowered due to an extension force of a compressed elastic spring and is locked to the outer housing.
Figure 4:
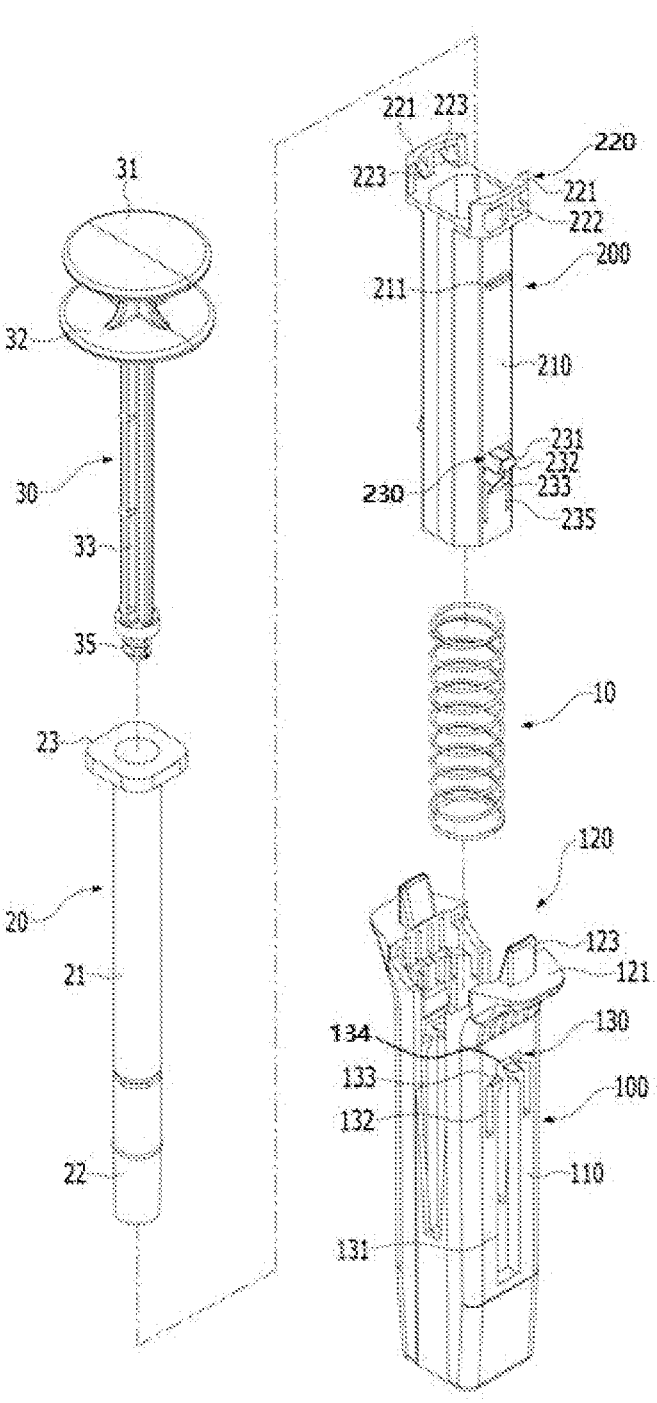
FIG. 4 is an exploded perspective view illustrating the disposable injection device with the locking structure to prevent reuse according to the present disclosure.
Figure 5:
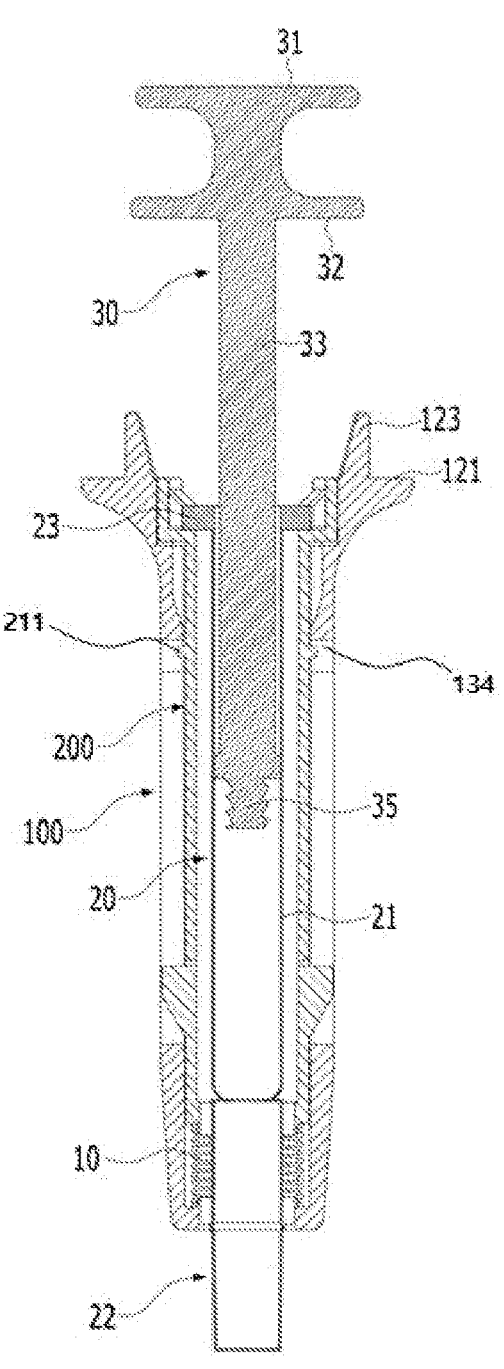
FIG. 5 is a cross-sectional view of FIG. 1.
Figure 6:
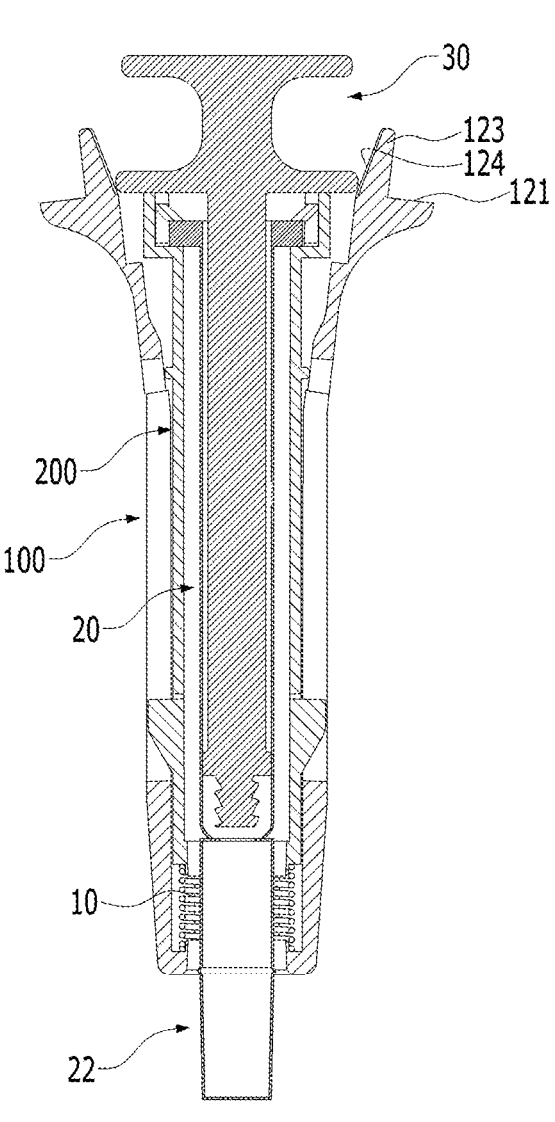
FIG. 6 is a cross-sectional view of FIG. 2.
Figure 7:
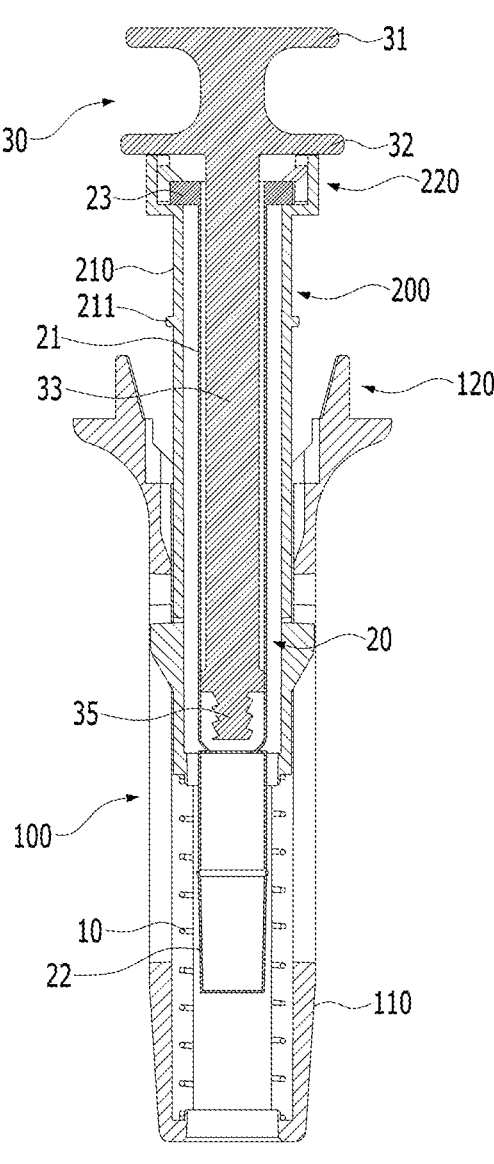
FIG. 7 is a cross-sectional view of FIG. 3.

A process of guiding separation between the locking module and the outer housing through additional lowering of the pressurizing piston unit 30 after an injection solution in the liquid cartridge 20 is completely injected through the pressurizing piston unit 30 will be described with reference to FIGS. 2 and 6.

The separation plate 32 of the pressurizing piston unit 30 may have a circular plate shape. When the pressurizing piston unit 30 is lowered, a separation distance between the pair of separation guide portions 120 is gradually increased through a process in which the separation plate 32 moves along the protrusion inclined surface 124 that is the inner surface of the separation guide protrusion 123. In the process, the unlocking protrusion 211 formed on the outer surface of the locking module 200 is separated from the protrusion mount groove 134, to temporarily release the fixing between the locking module 200 and the outer housing 100.

When the injection is completed and the pressing force on the pressurizing piston unit 30 is removed, the compressed elastic spring 10 is extended and the locking body 210 of the locking module 200 is raised and lowered. Once the locking module 200 is raised and lowered, the liquid cartridge 20 in which the cartridge body 21 is accommodated and the pressurizing piston unit 30 are simultaneously raised, and due to the raising of the cartridge body 21, the needle coupling portion 22 is drawn into the outer housing 100, thereby preventing exposure.

As such, after an injection solution is completely used, because the locking module 200 is locked to the outer housing 100, and even when the pressurizing piston unit 30 is pressed again, the locking module 200 raised and lowered after the injection solution is completely injected is locked to the outer housing 100, the pressurizing piston unit 30 may not be lowered and thus the needle coupling portion 22 to which the syringe needle is coupled may be prevented from being exposed from a lower end of the outer housing 100, and the injection solution may not be injected and thus the disposable syringe may be prevented from being reused.

As described above, the present disclosure may have a locking structure to prevent reuse in which, in a state where a locking module accommodating a liquid cartridge in which the injection of an injection solution is completed is additionally pressed, when the pressing force is removed, the pressed liquid cartridge is raised and lowered due to a restoring force of an elastic spring that is located in a compressed state at a lower end of the liquid cartridge and is locked to an outer housing, and thus the locking module accommodating the liquid cartridge is prevented from being further pressed. Also, the present disclosure may smoothly separate the locking module from the outer housing through a separation guide portion having a tapered shape and formed on an upper end of the outer housing through a pressure head constituting an upper portion of a pressurizing piston unit that is slidably coupled to the liquid cartridge and thus may reliably prevent reuse of a disposable syringe by enabling a syringe needle coupled to the lower end of the liquid cartridge to be drawn and located inside the outer housing.

The above description is merely illustrative of the technical idea of the present disclosure, and one of ordinary skill in the art to which the present disclosure pertains will be able to make various modifications and variations without departing from the essential characteristics of the present disclosure. Accordingly, the embodiments of the present disclosure should be considered in descriptive sense only and not for purposes of limitation of the scope of the present disclosure. The scope of the present disclosure is defined not by the detailed description of the present disclosure but by the appended claims, and all differences within the scope will be construed as being included in the present disclosure.

What is claimed is:

1. A disposable injection device, comprising:
an outer housing comprising:
a housing body having a hollow shape with an open upper portion;
a pair of separation guide portions constituting the open upper portion of the housing body, the pair of separation guide portions comprising a separation guide plate extending outward from an upper end of the housing body, a separation guide protrusion extending upward from a top surface of the separation guide plate; and
a reuse preventing portion formed on a side surface of the housing body;
a locking module configured to be position-changeably coupled in the outer housing, the locking module comprising:
a first locking body position-changeably located in the housing body;
a cartridge coupling portion constituting an upper portion of the first locking body;

a locking portion protruding from an outer surface of the first locking body; and
unlocking protrusions formed on both sides of the first locking body and spaced apart from the first locking body and located in a higher position in the first locking body than the locking portion;
an elastic spring located in a compressed state at a lower end of the locking module in the outer housing;
a liquid cartridge coupled to the locking module and configured for containing an injection solution therein; and
a pressurizing piston unit configured to pressurize the inside of the liquid cartridge and discharge the injection solution, the pressurizing piston unit comprising:
a pressure head;
a separation plate located in a plate shape under the pressure head and configured to allow the pair of separation guide portions to be opened outward; and
a plunger longitudinally formed from a lower portion of the pressure head and slidably coupled into the cartridge body,
wherein the reuse preventing portion includes:
a slide groove longitudinally formed in a vertical direction in the housing body to guide a movement when the locking module accommodated in the outer housing is temporarily released and raised;
protrusion grooves formed on both sides of an upper portion of the slide groove to be spaced apart from each other;
a lowering preventing protrusion configured to connect an upper end of the slide groove to an upper end of the protrusion groove, the lowering preventing protrusion configured to be bent inward and having a stepped shape with an inclined lower end, wherein the protrusion grooves are configured to secure a space for flexible movement of the lowering preventing protrusion; and
protrusion mount grooves formed over the lowering preventing protrusion and passing through the housing body, the protrusion mount grooves configured to prevent a raised locking module from being lowered again,
wherein the protrusion mount grooves are configured to be coupled to the unlocking protrusions to fix a position of the first locking body in the outer housing before the pressuring piston unit is lowered,
wherein, when the pressurizing piston unit is lowered, a separation distance between the pair of separation guide portions is gradually increased through a process in which the separation plate moves along an inner surface of the pair of separation guide protrusion so that the unlocking protrusions are separated from the protrusion mount grooves to temporarily release a fixing between the locking module and the outer housing.

2. The disposable injection device of claim 1, wherein the locking portion includes:
locking protrusions protruding from both side surfaces of the locking body to be located under the unlocking protrusions and be spaced apart from the unlocking protrusions;
a locking stepped portion constituting a lower end of the locking protrusion;
a second locking body extending downward from the locking protrusion based on the locking stepped portion; and protrusion moving grooves formed on both sides of the
locking body.

\* \* \* \* \*